Figure 1:
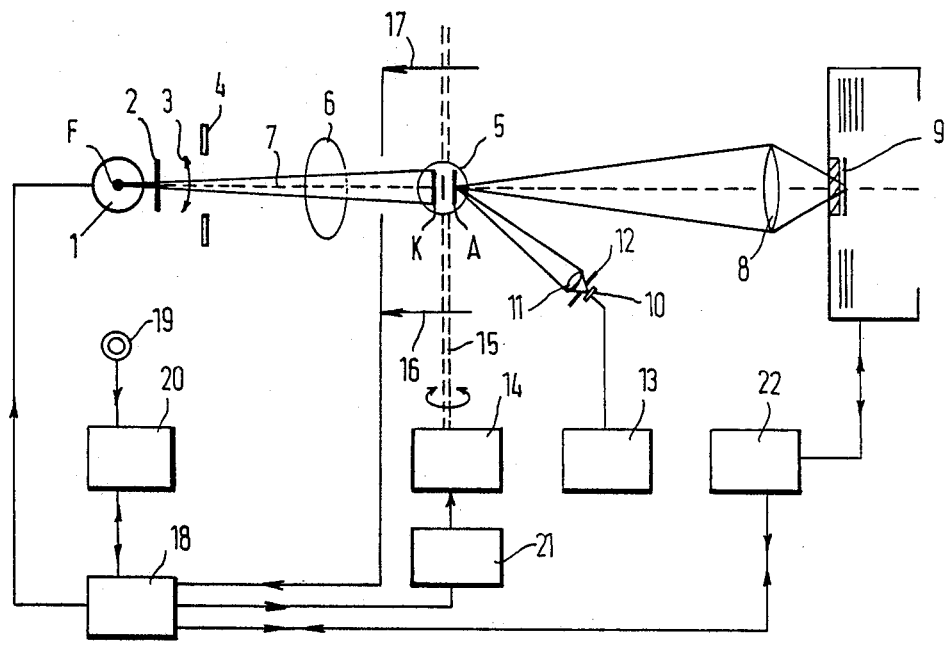

United States Patent [19]

Vlasbloem

[11] Patent Number: 4,803,714

[45] Date of Patent: Feb. 7, 1989

[54] METHOD FOR FORMING A RADIOGRAM USING SLIT-SCANNING RADIOGRAPHIC TECHNIQUES

[75] Inventor: Hugo Vlasbloem, Maasland, Netherlands

[73] Assignee: B. V. Optische Industrie "De Oude Delft", Delft, Netherlands

[21] Appl. No.: 648,707

[22] Filed: Sep. 7, 1984

[30] Foreign Application Priority Data

Sep. 13, 1983 [NL] Netherlands ............... 8303156

[51] Int. Cl.⁴ ............................................. G01N 23/04
[52] U.S. Cl. ....................................... 378/62; 378/108; 378/146
[58] Field of Search ............... 378/28, 40, 62, 146, 378/108

[56] References Cited

U.S. PATENT DOCUMENTS

| 2,837,657 | 6/1958 | Craig et al. | 378/146 |
| 3,766,387 | 10/1973 | Heffan et al. | 378/146 |
| 3,832,546 | 8/1974 | Morsell et al. | 378/146 |
| 3,924,133 | 12/1975 | Reiss | 378/62 |
| 4,433,430 | 2/1984 | Fredzell | 378/146 |

FOREIGN PATENT DOCUMENTS 0063644 11/1982 European Pat. Off. ............ 378/108

Primary Examiner—Carolyn E. Fields
Assistant Examiner—David P. Porta
Attorney, Agent, or Firm—Louis E. Marn

[57] ABSTRACT

There is disclosed a method for forming a radiogram of an object comprising the steps of energizing an X-ray source at a low level of radiation intensity wherein the X-ray source includes a slit diaphragm, pivoting the X-ray source during a first scanning of the object, moving an elongated X-ray detector in respect to the pivoting of the X-ray source to generate an output signal of intensity of the object during the first scanning thereof, measuring the output signal during at least a portion of said first scanning, energizing the X-ray source to a higher level of radiation intensity as determined by the output signal from the X-ray detector during the first scanning, pivoting the X-ray source during a second scanning of the object, moving the X-ray detector during the second scanning to generate a second output of radiation intensity and forming a radiogram from the second output signals.

1 Claim, 1 Drawing Sheet

METHOD FOR FORMING A RADIOGRAM USING SLIT-SCANNING RADIOGRAPHIC TECHNIQUES

This invention relates to a slit-scanning radiography apparatus, comprising a pivoting X-ray source having a slit diaphragm and X-radiation receiving means whose position, during operation, corresponds to the position of the X-ray source.

A similar apparatus is disclosed in the article entitled "Schlitzaufnahmetechnik mit mitgeführtem Strahler" by R. Moore and K. Amplatz, published in Elektromedica 1/81. The apparatus disclosed in this article comprises an X-ray source capable of irradiating a patient through a slit diaphragm, with a second slit diaphragm being disposed on the other side of the patient, which second slit diaphragm passes the radiation passed through the patient to an X-ray screen-film combination. In operation, the X-ray source is pivoted along with the first slit diaphragm and the second slit diaphragm, so that the patient is, as it were, scanned stripwise, and the picture to be formed is built-up in strips.

One advantage of the slit-scanning technique over and above the conventional technique is that a lower radiation dose can be used, so that the load of irradiation on the patient is less, and the effect of scattered radiation can be more effectively suppressed, so that clearer pictures can be obtained. A disadvantage of the known slit-scanning technique is that a second slit diaphragm is needed, and also an X-ray screen of large size.

It is an object of the present invention to improve the apparatus disclosed in the above article. For this purpose, according to the invention, an apparatus of the kind described is characterized in that the radiation-receiving means comprise an elongated X-ray detector movable transversely to its longitudinal direction and comprising an elongated cathode which, in operation, is irradiated by the X-ray source and converts incident radiation to electrons, which are moved by an electric field to an elongated anode.

One important advantage of the invention is that, in the X-ray detector, an intensification can be accomplished by a suitable selection of the electrical field intensity. As a consequence, a lower dose of radiation can be used.

It is a further object of the present invention to provide a method of using an apparatus according to the invention, in which the effect of the patient's dimensions on the exposure of a film is compensated for.

Figure 2:
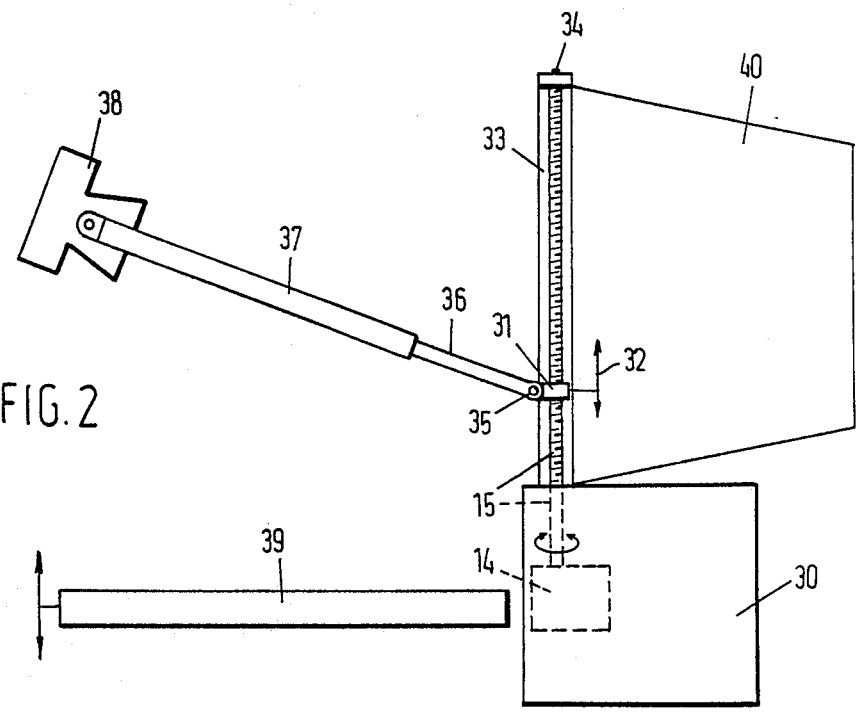

The invention will now be described in more detail with reference to the accompanying drawings, in which FIG. 1 diagrammatically shows an example of an apparatus according to the invention;

FIG. 2 diagrammatically shows an example of the construction of an apparatus according to the invention, except for the operating panel, which is generally arranged in a separate space.

One embodiment of an apparatus according to the invention is shown diagrammatically in FIG. 1.

An X-ray tube 1 is pivotable along with a slit diaphragm 2 about a shaft extending transversely to the plane of drawing, the axis of which shaft preferably intersects the X-ray focus F, mounted in a frame not shown. The pivotability of the X-ray source and the slit diaphragm is indicated by an arrow 3.

There is further provided a fixed field diaphragm 4.

The X-ray source is arranged in opposition to a case not shown, which may be closed with a plate of X-ray-permeable, but light-opaque material, and in which a special X-ray detector 5 is provided.

Between the case and the X-ray source is an open space, in which an object, such as a patient or other object 6 can be placed.

The X-ray detector 5 comprises an elongated housing extending in a direction transverse to the plane of drawing, in which housing a vacuum prevails, and in which are disposed an elongated cathode K and an elongated anode A parallel thereto. The slit diaphragm 2 has such slit dimensions that the X-ray beam 7 passed just exposes the cathode K.

The cathode comprises a layer of material which converts incident radiation into light, and a layer of material from which, under the influence of light, electrons are emitted. The emitted electrons are accelerated under the influence of an electric field established between the cathode and the anode, and passed to the anode, which under the influence of these electrons forms a light image. The housing of the X-ray detector may consist of glass, or of another material, provided the cathode can be reached by X-rays and, on the anode side, if necessary, a light-permeable window is present. It is also possible for the anode to be designed, for example, by using a so-called CCD-array, so that is provides an image information containing electrical signal that can be stored in a memory for further processing at a later stage.

A detector tube as referred to hereinbefore is, in principle, described in Dutch patent application No. 79,00878.

In operation, the X-ray image intensifier moves in synchronism with the sweep of the X-ray source, so that the X-ray beam falls at all times on the cathode.

It is noted that the X-ray source and the X-ray detector are shown in the figure in one of the intermediate positions they occupy as a picture is taken. In the inoperative position, the X-ray source is directed diagonally downwardly or diagonally upwardly, and the X-ray detector is in a corresponding position.

If an anode forming a light image is used, the light image formed by the anode in operation is depicted on a film 9 by means of an optical system 8. The optical system is disposed so as to be stationary, and the film is also stationary as a picture is taken.

The use of a moving elongated, if desired intensifying, X-ray detector results in several advantages. Thus a second slit diaphragm of large dimensions moving along with the X-ray source is no longer necessary. Also, it is sufficient to have a relatively small film area (for example 10×10 cm). The exposure of the film can further be controlled in two ways, namely, by controlling the energizing current of the X-ray source itself and by controlling the voltage between the anode and the cathode of the X-ray detector. Finally, the use of an intensifying X-ray detector makes it possible to use very low X-ray doses.

In order that an optimum X-ray dose may be selected for a radiogram of an individual patient, according to the invention there is first made a measuring exposure.

In making a measuring exposure, after the patient or the object to be X-rayed has been placed in position, the X-ray source is energized so that it emits radiation with an intensity lower by a factor of about 10 than the average intensity used for a normal exposure. The X-ray source moves, for example, from the bottom angular position to the top angular position, with the X-ray image intensifier moving along with it correspondingly.

During a certain part of the X-ray image intensifier's path (the measuring field), the average level of the light generated by the anode of the X-ray detector is measured by means of a photometer 10. If an anode is used which generated an electrical signal, an apparatus indicating the average intensity of the electrical signal can be used instead of a photometer. The size of the measuring field can be selected as desired. In experiments, a measuring field of 10×20 cm has proved satisfactory. As, for example for thorax exposures, the X-ray detector should be at least 40 cm long, the measuring field may accordingly be narrower than the field covered by the X-ray detector without any objections.

In front of the photometer, a lens system 11 and a diaphragm 12 may be placed. The photometer 10 is connected to an instrument 13 to be read. Depending on the light value measured, the X-ray dose needed for the actual exposure can now be set at an optimum value either manually or automatically. In the latter case, the output signal from the photometer control the voltage of the X-ray detector or the current through the X-ray tube. The readable instrument then only serves for monitoring purposes and, if desired, may be omitted. It is noted that the measuring exposure takes place without a film 9. The film is not supplied until the actual exposure. When the X-ray source is properly set, the X-ray source is pivoted in the opposite direction, with the X-ray detector moving along with it for making the actual radiogram.

For monitoring purposes, the photometer can be switched on again during the actual exposure. For this purpose, after the measuring exposure, the photometer is first set in the zero position, and also set in a less sensitive mode. After the actual exposure or before the next measuring exposure, too, the photometer is re-set in the zero position.

Experiments have shown that the making of an exposure, including the measuring exposure, takes about ten sec.

In the arrangement shown, the X-ray detector moves in a vertical plane by means of a vertical threaded spindle 15 driven by an electric motor 14. The spindle 15 is connected to a holder, not shown, for the X-ray detector, which holder is provided with a portion cooperating with the threaded spindle.

As an exposure is made, the X-ray detector, and hence the motor must have a very constant velocity. Moreover, after being energized, the motor must reach the operating velocity very fast, but after the exposure has been made, it must also stop very fast. Accordingly, the motor must have a high initial torque and a short stopping distance.

In order to meet these requirements, use is made of a disk-armature motor with a starting time and a stopping time of about 150 msec and an operative speed of about 2500 rpm. Furthermore, the motor preferably has two directions of rotation, so that the threaded spindle 15 can be fixedly connected to the motor shaft.

The spindle 15 is further coupled, by means of a rod provided with a threaded portion, not shown in FIG. 1, to the X-ray source to enable the latter to perform the required sweep.

Provided along the path to be covered by the X-ray detector, in the vicinity of the two ends, are micro-switches, shown diagrammatically at 16 and 17. At both 16 and 17 there may be provided more than one switch ($S_1$, $S_4$ and $S_2$, $S_3$, respectively). These switches are connected to a control unit 18, which in turn is connected to an operating knob 19 and an adjusting device 20 for the energizing current for the X-ray source.

Switches $S_1$, $S_4$ and $S_2$, $S_3$, respectively, serve, among other purposes, to switch off the X-ray source, via control unit 18, after a downward and an upward sweep, respectively, of the X-ray detector; to switch off the energization of the motor, which takes place by a motor energizing circuit 21; and to bring the motor energizing circuit into such a state that during the next sweep of the X-ray detector the motor turns in the correct direction.

Furthermore, by means of the micro-switches and a film transport control device 22, it can be accomplished that after a measuring exposure a new film is supplied.

As conventional with radiography apparatuses, the unit is equipped with various signal lamps, not shown, which for example indicate whether a film has actually been supplied, whether the film magazine is empty, what is the position of the photometer, whether a patient identifying card, also to be photographed, has been placed in the holder provided for that purpose, and the like.

The motor 14 is placed in a mounting bracket 30, which may also house the energizing circuits of the unit. The threaded spindle 15 connected to the motor extends vertically upwardly and cooperates with a nut element 31 which, when the motor rotates, moves upwardly or downwardly, as indicated by an arrow 32. The threaded spindle extends along a flat vertical case 33, which contains the X-ray image intensifier in a horizontal position and is journalled at the top of the case in a bearing 34. The X-ray detector is connected to the nut element.

The nut element is further connected by means of a hinge 35 to a linkage consisting of two telescoping parts 36,37. The other end of the linkage is fixedly connected to a housing 38 accommodating the X-ray source and the slit diaphragm.

Placed on the side of bracket 30 facing the X-ray source is a platform 39, movable up and down, and serving to bring a patient at the desired level in front of the flat case 33.

Secured to the side of case 33 remote from the X-ray source is a housing 40 accommodating the optical system, the photometer, a film magazine, the film transport mechanism and the patient identifying card holder and the like.

It is observed that many variants of the arrangement shown in FIG. 2 are possible. Thus, for example, the arrangement may be such that a patient should lie down in it. Also, the coupling of the threaded spindle 15 to the housing 38 of the X-ray source may be realized in quite a different manner. Thus, for example, the linkage, described by way of example, may be omitted if the sweep of the X-ray source is effected by a separate motor driven so that the X-ray beam continues to impinge on the elongated X-ray detector during the translation thereof. The two motors should then be synchronized, which can be accomplished by means of a servo mechanism or by means of a micro-processor to which information is supplied about the exposure time and the distance between the X-ray focus and the X-ray detector.

Furthermore, the micro-switches may be arranged in the vicinity of the housing of the X-ray source, and be operated by the sweep thereof.

These and other modifications will readily occur to those skilled in the art after reading the foregoing without departing from the scope of the invention.

I claim:
1. A method for forming a radiogram of an object, which comprises the steps of:
   (a) energizing an X-ray source to a low level of radiation intensity, said X-ray source including a slit diaphragm;
   (b) pivoting said X-ray source during a first scanning of said object;
   (c) moving an elongated X-ray detector along a position corresponding to a position of said X-ray source during said first scanning thereby to generate output signals of radiation intensity;
   (d) measuring said output signals during at least a portion of said first scanning;
   (e) energizing said X-ray source to a higher level of radiation intensity as determined by step (d) to form a radiogram;
   (f) pivoting said X-ray source during a second scanning of said object at said higher level of radiation intensity;
   (g) moving said elongated X-ray detector along said position corresponding to said position of said X-ray source during said second scanning thereby to generate second output signals of radiation intensity; and
   (h) forming said radiogram from said second output signals.

* * * * *